United States Patent
Dakka et al.

(10) Patent No.: US 10,919,830 B2
(45) Date of Patent: Feb. 16, 2021

(54) LAYERED CATALYST LOADING FOR SYNTHESIS GAS CONVERSION

(71) Applicant: ExxonMobil Research and Engineering Company, Annandale, NJ (US)

(72) Inventors: Jihad M. Dakka, Whitehouse Station, NJ (US); Michael J. Sikorsky, Easton, PA (US); Aruna Ramkrishnan, Bridgewater, NJ (US); Chuansheng Bai, Phillipsburg, NJ (US); Anita S. Lee, Spring, TX (US); Preeti Kamakoti, Berkeley Heights, NJ (US); Anjaneya S. Kovvali, Herndon, VA (US); Jenna L. Walp, Bethlehem, PA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 16/738,624

(22) Filed: Jan. 9, 2020

(65) Prior Publication Data
US 2020/0231525 A1 Jul. 23, 2020

Related U.S. Application Data

(60) Provisional application No. 62/794,137, filed on Jan. 18, 2019.

(51) Int. Cl.
| | |
|---|---|
| C07C 41/09 | (2006.01) |
| C07C 29/00 | (2006.01) |
| C07C 31/00 | (2006.01) |
| C07C 43/00 | (2006.01) |
| B01J 8/00 | (2006.01) |
| B01J 8/02 | (2006.01) |
| C07C 29/153 | (2006.01) |
| B01J 20/02 | (2006.01) |
| B01J 21/04 | (2006.01) |
| B01J 23/80 | (2006.01) |
| C07C 31/04 | (2006.01) |
| C07C 43/04 | (2006.01) |

(52) U.S. Cl.
CPC ............... *C07C 41/09* (2013.01); *B01J 8/008* (2013.01); *B01J 8/02* (2013.01); *C07C 29/153* (2013.01); *B01J 20/0248* (2013.01); *B01J 21/04* (2013.01); *B01J 23/80* (2013.01); *B01J 2208/00805* (2013.01); *B01J 2208/025* (2013.01); *B01J 2208/027* (2013.01); *C07C 31/04* (2013.01); *C07C 43/043* (2013.01)

(58) Field of Classification Search
CPC ........... C07C 41/09; C07C 29/153; B01J 8/02
See application file for complete search history.

(56) References Cited

U.S. PATENT DOCUMENTS

| | | |
|---|---|---|
| 4,016,218 A | 4/1977 | Haag et al. |
| 4,696,732 A | 9/1987 | Angevine et al. |
| 4,835,329 A | 5/1989 | Harandi et al. |
| 5,019,663 A | 5/1991 | Chou et al. |
| 2015/0045456 A1 | 2/2015 | Schoedel et al. |
| 2016/0102031 A1 | 4/2016 | Du et al. |
| 2018/0002265 A1 | 1/2018 | Wright et al. |

FOREIGN PATENT DOCUMENTS

| | | |
|---|---|---|
| EP | 1010683 A1 | 6/2000 |
| GB | 1398696 A | 6/1975 |

OTHER PUBLICATIONS

The International Search Report and Written Opinion of PCT/US2020/012915 dated May 12, 2020.

*Primary Examiner* — Sikarl A Witherspoon
(74) *Attorney, Agent, or Firm* — Liza Negron (57) ABSTRACT

Systems and methods are provided for conversion of gas phase reactants including CO and $H_2$ to $C_{2+}$ products using multiple catalysts in a single reactor while reducing or minimizing deactivation of the catalysts. Separate catalysts can be used that correspond to a first catalyst, such as a catalyst for synthesis of methanol from synthesis gas, and a second catalyst, such as a catalyst for conversion of methanol to a desired $C_{2+}$ product. The separate catalysts can be loaded into the reactor in distinct layers that are separated by spacer layers. The spacer layers can correspond to relatively inert particles, such as silica particles. Optionally, the spacer layer can include an adsorbent, such as boron supported on alumina or boron carbide particles. The adsorbent can be suitable for selective adsorption of the one or more reaction products (such as one or more reaction by-products), to allow for further reduction or minimization of the deactivation of the conversion catalysts.

23 Claims, 8 Drawing Sheets

LAYERED CATALYST LOADING FOR SYNTHESIS GAS CONVERSION

CROSS-REFERENCE TO RELATED APPLICATIONS

This application claims the benefit of U.S. Provisional Application No. 62/794,137, filed on Jan. 18, 2019, the entire contents of which are incorporated herein by reference.

FIELD

This invention relates to stacked bed catalyst configurations for conversion reactions involving multiple catalysts, such as conversion of synthesis gas to dimethyl ether in a single reactor.

BACKGROUND

Conversion of methane to higher hydrocarbon products is a desirable process for a variety of reasons. In addition to the abundance of available methane in known petroleum reserves, using methane as a starting point for formation of higher hydrocarbons can potentially provide flexibility in producing desired or needed hydrocarbon products. Unfortunately, the currently known pathways for upgrading of methane to $C_{2+}$ products can be difficult to implement on a commercial scale, due in part to high costs and/or low yields.

One potential pathway for upgrading of methane is to convert the methane to dimethyl ether, such as by first forming synthesis gas, then forming methanol from the synthesis gas, followed by conversion of at least a portion of the methanol to dimethyl ether. U.S. Patent Application Publication 2015/0045456 describes an integrated process for conversion of methane to dimethyl ether via synthesis gas and methanol intermediates. In addition to the high capital and/or operating cost for the initial conversion of methane to synthesis gas, the yields for conversion of synthesis gas to dimethyl ether via methanol are relatively low.

Conventionally, the conversion of synthesis gas to dimethyl ether is performed in a plurality of reactors, with the catalyst for synthesis of methanol from synthesis gas being located in separate reactor(s)/stage(s) from the catalyst for conversion of methanol to dimethyl ether. U.S. Patent Application Publication 2018/0002265 describes an example of a reactor for conversion of synthesis gas to dimethyl ether in a single step, using a bifunctional catalyst. Unfortunately, such single stage conversion methods for conversion of synthesis gas to dimethyl ether can tend to suffer from short catalyst lifetimes. This can result in a need to have to regenerate the catalyst on a more frequent basis than is desirable in a commercial setting.

It would be desirable to use a conversion method for conversion of synthesis gas to dimethyl ether that could allow the conversion to take place in a single step, while avoiding the difficulties associated with rapid catalyst deactivation.

SUMMARY OF THE INVENTION

In some aspects, a method for converting synthesis gas to $C_{2+}$ products is provided. The method includes exposing a feed comprising CO and $H_2$ to a plurality of layered catalyst groupings under conversion conditions to form a conversion effluent comprising $C_{2+}$ products. A catalyst grouping can include a) a methanol synthesis catalyst layer including methanol synthesis catalyst particles; b) a second spacer layer including second layer spacer particles; c) an acidic catalyst layer including acidic catalyst particles; and d) a fourth spacer layer including fourth layer spacer particles. In such aspects, a combined weight of the methanol synthesis catalyst particles in the methanol synthesis catalyst layers can correspond to a first weight, and a combined weight of the second layer spacer particles in the second spacer layers can correspond to 10% to 110% of the first weight. Additionally or alternately, in such aspects a combined weight of the acidic catalyst particles in the acidic catalyst particle layers can correspond to a third weight, and a combined weight of the fourth layer spacer particles in the fourth spacer layers can correspond to 10% to 110% of the first weight.

In some aspects, a method for converting gas phase reactants in multiple steps is also provided. The method can include exposing a feed comprising CO and $H_2$ to a plurality of layered catalyst groupings under conversion conditions to form a conversion effluent comprising $C_{2-}$ products. The exposing of the feed to a layered catalyst grouping can include: a) exposing the feed to a first catalyst layer including first catalyst particles under the conversion conditions to form a first intermediate effluent including a first plurality of reaction products, the first catalyst particles optionally corresponding to methanol synthesis catalyst particles; b) exposing the first intermediate effluent to a second spacer layer including second layer spacer particles under the conversion conditions to form a second intermediate effluent, a concentration of at least one reaction product of the plurality of reaction products in the second intermediate effluent being reduced by 10 wt % or more relative to a weight of the at least one reaction product in the first intermediate effluent; c) exposing the second intermediate effluent to a third catalyst layer including third catalyst particles under the conversion conditions to form a third intermediate effluent comprising a third plurality of reaction products, the conversion conditions being effective for conversion of one or more reaction products from the first plurality of reaction products to form the third plurality of reaction products, the third catalyst particles optionally corresponding to acidic catalyst particles; and d) exposing the third intermediate effluent to a fourth spacer layer including fourth layer spacer particles, a concentration of at least one reaction product of the third plurality of reaction products in the fourth intermediate effluent being reduced by 10 wt % or more relative to a weight of the at least one reaction product in the third intermediate effluent. In such aspects a combined weight of the first catalyst particles in the first catalyst layers can correspond to a first weight, and a combined weight of the second layer spacer particles in the second spacer layers can correspond to 10% to 110% of the first weight. Additionally or alternately, in such aspects a combined weight of the third catalyst particles in the third catalyst layers can correspond to a third weight, and a combined weight of the fourth layer spacer particles in the fourth spacer layers can correspond to 10% to 110% of the third weight.

DETAILED DESCRIPTION

In various aspects, systems and methods are provided for conversion of gas phase reactants including CO and $H_2$ to $C_{2+}$ products in a single reactor containing multiple catalysts while reducing or minimizing deactivation of the catalysts. Separate catalysts can be used that correspond to a first catalyst, such as a catalyst for synthesis of methanol from synthesis gas (syngas), and a second catalyst, such as a catalyst for conversion of methanol to a desired $C_{2+}$ product. Examples of $C_{2+}$ products can include oxygenates such as dimethyl ether, ethylene, propene, and other $C_{2+}$ olefins, and/or aromatic hydrocarbons. The separate catalysts can be loaded into the reactor in distinct layers that are separated by spacer layers. From a catalytic standpoint, the spacer layers can correspond to relatively inert particles, such as silica particles. However, the particles in the spacer layers can preferably be suitable for binding with one or more reaction products (such as reaction by-products) in order to reduce or minimize deactivation of at least one type of conversion catalyst particle. Optionally, the spacer layer can include an adsorbent, such as boron supported on alumina or boron carbide particles. The adsorbent can be suitable for selective adsorption of the one or more reaction products (such as one or more reaction by-products), to allow for further reduction or minimization of the deactivation of the conversion catalysts.

In addition to reducing or minimizing deactivation, the layered catalyst configuration can also facilitate regeneration of the separate catalysts. The conditions for effective regeneration of a methanol synthesis catalyst can be substantially different from the conditions for regeneration of a methanol conversion catalyst. By using multiple catalyst layers with spacer materials, when it is time to remove the catalyst for regeneration, the layers can be removed without mixing the catalyst particles. This can allow the catalyst particles to be separately regenerated under the appropriate conditions for each type of catalyst. This is in contrast to a hybrid catalyst configuration, where multiple catalysts are included in a single layer. It is noted that the size and/or density of the particles in the spacer layers can optionally be selected to be different from one or more of the various types of catalyst particles. This can facilitate separating the spacer particles from the catalyst particles prior to regeneration.

More generally, a layered catalyst configuration in a fixed bed reactor can allow various other types of conversion reactions to be performed using multiple catalysts. For example, conversion of synthesis gas to other products in a single reactor can also be performed, such as conversion of synthesis gas to olefins, synthesis gas to aromatics, or synthesis gas to gasoline. These additional conversion reactions can be performed by varying the temperature, pressure, and/or methanol conversion catalyst in the reactor, with a similar layered structure for the synthesis gas conversion catalyst and the methanol conversion catalyst. Optionally, the methanol synthesis catalyst can also be modified.

Conversion of synthesis gas to various products is desirable for a variety of reasons. Some reasons include the abundance of available methane. One of the more readily accessible pathways for converting methane to higher hydrocarbons is to first reform the methane to form synthesis gas. The synthesis gas can then be converted to methanol, which can then be used to form a variety of potential products.

After conversion of synthesis gas to methanol, it can be desirable to further convert the methanol to dimethyl ether. For many types of reactions involving methanol conversion, such as conversion of methanol to olefins, aromatics, and/or gasoline, the amount of heat generated during methanol conversion can be substantial. For many methanol conversion reaction schemes, dimethyl ether can be used in place of and/or in addition to methanol. The conversion of methanol to dimethyl ether is also exothermic. By converting at least a portion of the methanol to dimethyl ether prior to a conversion process, the amount of heat generated during the conversion process can be mitigated.

Figure 1:
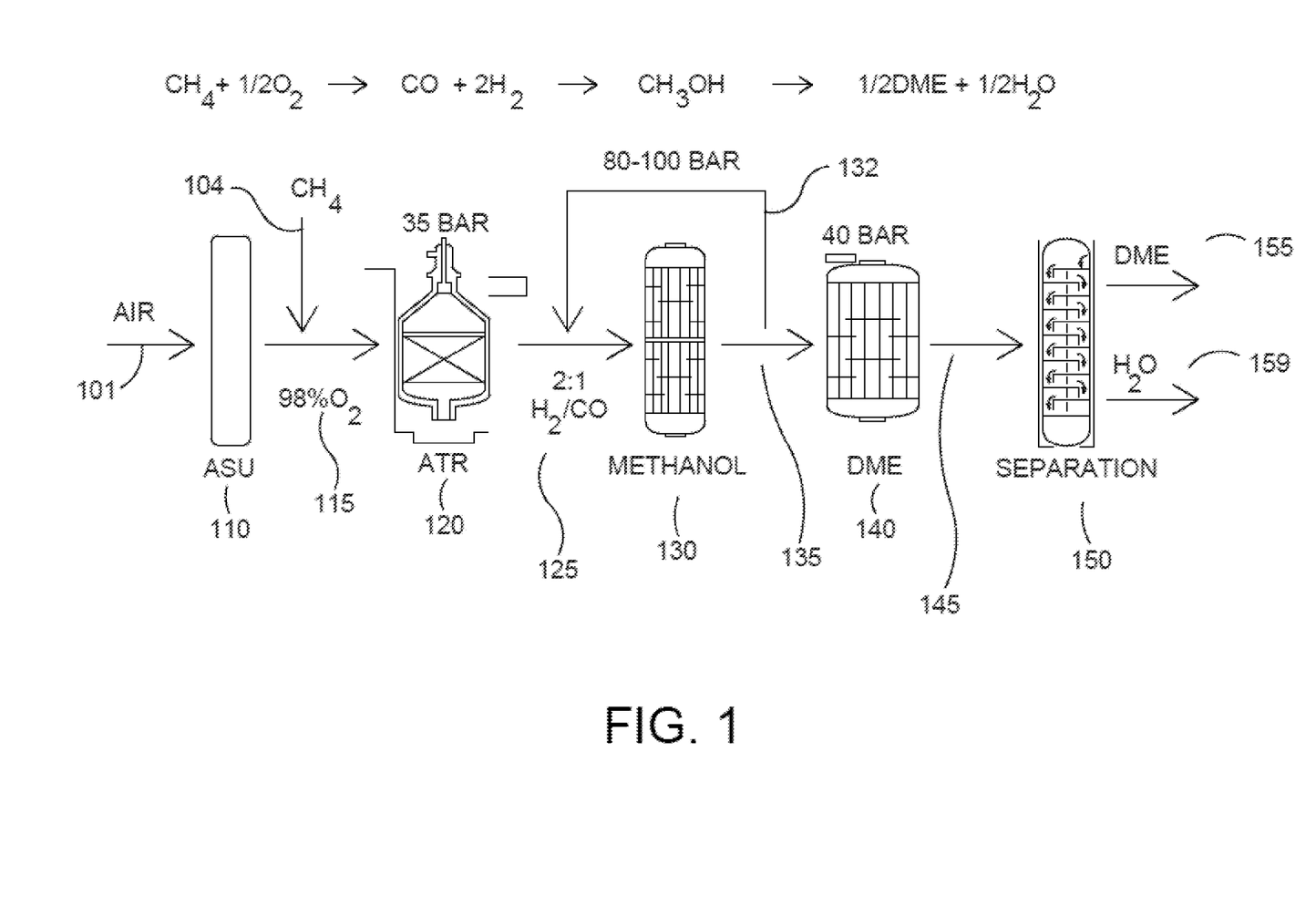
FIG. 1 shows an example of an overview of a reaction system for converting methane into dimethyl ether.

FIG. 1 shows an overview of a reaction system suitable for conversion of methane to dimethyl ether via synthesis gas and methanol intermediates. In the example configuration shown in FIG. 1, air 101 is introduced into an air separation unit 110 to produce an oxygen-containing stream 115 having a relatively high purity, such as 98 vol % $O_2$. Methane 104 can be added to the oxygen-containing stream 115 prior to entering a reforming stage 120, such as an autothermal reformer or a steam reformer. In some aspects, the reforming stage can be implemented as a reverse flow reactor. The reforming stage 120 can produce a syngas stream 125. After optionally adjusting the $H_2$ to CO ratio, the syngas stream 125 can be combined with a recycle stream 132 prior to entering methanol synthesis stage 130 for conversion of synthesis gas to methanol. The yield of methanol from methanol synthesis stage 130 can be relatively low, so unreacted synthesis gas from conversion stage 130 can be used to form a recycle stream 132. The methanol effluent 135 from the conversion stage 130 can then be passed into a methanol conversion stage 140. In the configuration shown in FIG. 1, the methanol conversion stage 140 is shown as a stage for conversion of methanol to dimethyl ether. In other aspects, any convenient type of methanol conversion stage can be used, such as conversion of methanol to olefins, aromatics, and/or other products such as naphtha with a desirable octane content. The effluent 145 from methanol conversion stage 140 can then be passed into one or more separation stages 150 for separation of products. In the configuration shown in FIG. 1, the separation stage 150 can be used to separate dimethyl ether 155 and water 159 from the effluent 145.

The configuration shown in FIG. 1 requires significant investment for the air separation unit and the autothermal reformer (or other reforming stage). The reforming of methane to syngas can also be performed with the addition of steam instead of oxygen, commonly known as steam methane reforming, in addition to other methods of generating synthesis gas from methane. Similarly, the feed to the reforming section can be methane or combination of methane and other components found in natural gas streams, such as ethane, propane, butane, and/or other hydrocarbons. More generally, the feed to the reforming section can be any type of hydrocarbon feed (including feeds containing hydrocarbonaceous compounds with heteroatoms different from carbon and hydrogen) that is generally considered suitable as a feed for reforming. Unfortunately, the yield from a methanol synthesis process is typically rather low, such as roughly 20% conversion of synthesis gas to methanol per pass. This is due in part to equilibrium limitations in the methanol synthesis process. As a result, the recycle loop from the outlet of the methanol synthesis process can correspond to up to 75% or more of the total feed into the methanol synthesis process. This can add further substantial costs when attempting to implement a configuration such as FIG. 1.

One option for overcoming the equilibrium limitations on the methanol synthesis reaction can be to have the methanol conversion catalyst co-located with the methanol synthesis catalyst. This can allow the methanol generated by the methanol synthesis catalyst to be consumed in-situ by the conversion catalyst. Because the methanol is being consumed in-situ, additional methanol synthesis can potentially take place under the equilibrium constraints. Conventionally, this has been attempted using a bi-functional catalyst or using a mixed catalyst bed. This can be effective for limited time periods, and can potentially increase per pass conversion of the synthesis gas from roughly 20% to up to roughly 70%. However, attempting to combine a methanol synthesis catalysts with a methanol conversion catalyst can pose a variety of challenges.

Some difficulties with using a bi-functional catalyst or mixed bed of methanol synthesis catalyst and methanol conversion catalyst can be related to loss of catalyst lifetime. Methanol synthesis catalysts are typically metal catalysts, such as catalysts including a combination of copper, zinc oxide, and aluminum oxide. By contrast, methanol conversion catalysts are typically acidic catalysts, such as alumina or catalysts including a zeolitic framework structure. Having these distinct types of catalysts co-located in the same reaction environment can potentially lead to deactivation of one or both of the catalysts. For the acidic catalysts, possible deactivation mechanisms can include acid neutralization due to migration of metals from the metal oxide catalyst; dealumination of zeolitic catalysts; and/or coke formation on the catalyst. For the metal catalyst, possible deactivation mechanisms can include metal sintering, resulting in lower Cu metal dispersion and/or loss of active sites; oxidation of Cu by oxygen-containing by-products (e.g., formic acid, acetic acid) generated by the syngas-to-methanol reaction; and/or coke formation on the surface of the metal catalyst, which can make active sites inaccessible. Unfortunately, some deactivation mechanisms for each catalyst can be enhanced by the other catalyst. For example, when the two types of catalysts are co-located, metals from the metal catalyst can be available for migration to the acidic catalyst, which can lead to loss of acidity. This can lead to rapid loss of activity for formation of dimethyl ether (or other desired methanol conversion products) when the two types of catalyst functionality are co-located. Additionally, the metal catalyst is typically stable in reaction environments where the temperature is 280° C. or less and substantially no water. These problems can be further compounded due to the fact that the selectivity for dimethyl ether is less than 100%. At least some of the oxygenates formed by the methanol conversion catalyst correspond to formic acid and acetic acid. When these acids are in the environment with the metal catalyst, the acids can facilitate migration of metal from the metal catalyst to the acidic catalyst.

Other difficulties can be related to regeneration of the catalysts after deactivation. When the metal catalysts and acidic catalysts are co-located as a mixture in a catalyst bed, there is not a practical solution for separating the catalysts to allow for separate regeneration. Unfortunately, the regeneration conditions for the metal catalyst and the acidic catalyst are substantially different, due to the differing nature of the goal of regeneration for each type of catalyst. For example, the regeneration conditions for a methanol synthesis catalyst typically involve exposing the catalyst to a reducing environment, such as exposing the catalyst to an environment including $H_2$ at temperatures between 200° C. and 400° C. This type of regeneration condition, however, is not effective for regeneration of the acidic catalyst, which typically involves removal of coke from the acidic catalyst. Instead, the acidic catalyst can typically be regenerated by exposing the catalyst to an oxidizing environment at temperatures of 500° C. or more. The coke can be combusted and/or removed from the acidic catalyst under the oxidizing conditions. However, such regeneration conditions can be detrimental for the metal catalyst, such as by causing metal sintering (loss of metal dispersion) and by further oxidizing the metal.

In various aspects, the above difficulties with co-location of methanol synthesis functionality with methanol conversion functionality can be overcome by using a layered catalyst configuration. It has been unexpectedly discovered that the equilibrium constraints on methanol production can be overcome while reducing or minimizing catalyst deactivation by using alternating layers of methanol synthesis catalyst and methanol conversion catalyst, with layers of spacer material in between each catalyst layer.

Including at least two layers of each type of catalyst, or preferably at least four, or at least six, such as up 8 or up to 10, can be beneficial for enabling increased conversion while reducing or minimizing catalyst deactivation. For example, due to the relatively rapid equilibrium, a thin layer of methanol synthesis catalyst can be suitable for building up a substantial amount of methanol, although the equilibrium value may not be achieved. This methanol can then flow through the spacer layer to the methanol conversion catalyst. The methanol conversion catalyst can convert the methanol to dimethyl ether (or another desired product). Because the methanol conversion occurs in a separate layer, the amount of coke deposited on a metal catalyst is reduced or minimized. The effluent, now depleted in methanol, can continued to contact the next methanol catalyst and again build up the methanol concentration. This can continue until the effluent passes through the final bed of methanol conversion catalyst. By using alternating layers, an increased amount of methanol can be created from the synthesis gas without exceeding the equilibrium amount. This increases the amount of methanol available for conversion.

In order to achieve the benefits of the layered configuration, the layers of catalyst can be relatively thin. Conventionally, multiple stacked beds have been used, such as stacked beds of catalyst for hydrotreating reactions. However, in such conventional configurations, the intermediate product streams between the stacked beds are taken out of the reactor, cooled or heated, and then reintroduced into the reactor prior to contacting the catalyst in the next bed. This additional withdrawal/heating/cooling of the intermediate products is typically performed as a means to improve the performance of the overall reactor, such as by improving heat management or by improving mass transfer. In a conventional reactor where catalysts are co-located, one of the benefits of co-location is that the methanol conversion catalyst is present to consume methanol in the same region where the methanol is created. This can help overcome the equilibrium limitations on methanol synthesis.

To achieve a similar benefit in a layered system, it has been discovered that catalyst layers can be used where the space velocity for individual catalyst layers for at least one of the catalysts is substantially greater than conventional space velocities. For example, the weight hourly space velocity of feed relative to the total amount of catalyst in the layers can be on the order of 0.5 hr$^{-1}$ to 10 hr$^{-1}$, but each type of catalyst can be divided between two or more distinct layers. This means that there are at least four total layers of catalyst. If the catalyst layers are roughly equal in size, this corresponds to weight hourly space velocities of 2.0 hr$^{-1}$ or more, and possibly much higher as more layers are used. For example, for at least one of the catalyst types, the weight hourly space velocity for the individual catalyst layers can be 5.0 hr$^{-1}$ or more, or 10 hr$^{-1}$ or more, or 20 hr$^{-1}$ or more, such as up to 50 hr$^{-1}$ or possibly still higher. In terms of gas hourly space velocities (comparison of volume of CO in synthesis gas with catalyst volume), the gas hourly space velocity relative to the total catalyst load can be between 500 hr$^{-1}$ and 10000 hr$^{-1}$, or 1000 hr$^{-1}$ and 8000 hr$^{-1}$. When at least four layers of each catalyst are used, this can correspond to a gas hourly space velocity for the individual layers of 4000 hr$^{-1}$ or more, or 8000 hr$^{-1}$ or more, or 20000 hr$^{-1}$ or more, or possibly much higher as more layers are used.

Optionally but preferably, the space velocity and/or the thickness of the catalyst layers can be selected so that the reactions in each layer can reach an equilibrium level. For example, the conversion of synthesis gas to methanol corresponds to an equilibrium process. The thickness of one or more (such as a plurality) of the methanol synthesis catalyst layers can be sufficiently large and/or the layer space velocity can be sufficiently low so that the equilibrium level of methanol is achieved within the feed prior to exiting the methanol synthesis catalyst layer. Additionally or alternately, the thickness of one or more (such as a plurality) of the methanol conversion catalyst layers can be sufficiently large and/or the layer space velocity can be sufficiently low so that the equilibrium level of dimethyl ether is achieved within the feed prior to exiting the methanol conversion catalyst layer.

Additionally or alternately, the feed can be exposed to the catalysts in the plurality of catalyst layers without removal of intermediate products from the reactor. For example, the feed can be exposed to four or more layers of catalyst without removal of intermediate product, or six or more layers, or eight or more layers.

It is noted that in some aspects, the thickness of the catalyst layers for at least one type of catalyst may vary within the reactor. In situations where the catalyst layers have variable thickness for a given type of catalyst, it can be beneficial to have at least 4 layers for at least one type of catalyst where the layer thickness for the catalyst layers results in a weight hourly space velocity and/or gas hourly space velocity as described above.

The layered catalyst configuration can also be beneficial for catalyst regeneration. When it is time to regenerate the catalyst in the reactor, the catalyst can be removed layer by layer. This can be achieved by draining the catalyst from the bottom of the reactor, scooping a catalyst layer from the top of the reactor, or by any other convenient method. The presence of the spacer layers means that control over the catalyst removal does not have to be precise in order to maintain separation of the methanol synthesis catalyst and the methanol conversion catalyst. Silica particles are an example of a suitable particle for the spacer layer.

The spacer layers can provide a physical separation between catalyst layers that can reduce or minimize deactivation. Additionally or alternately, the spacer layers can provide at least some ability to reduce the concentration of one or more reaction products that can contribute to deactivation. For example, in addition to producing methanol, the conditions for methanol synthesis can also result in production of small carboxylic acids, such as formic acid and/or acetic acid. In some aspects, by passing the effluent from a methanol synthesis layer through a spacer layer, the concentration of at least one reaction product (such as formic acid and/or acetic acid) in the methanol synthesis effluent can be reduced by 10% or more (20% or more), relative to the weight of the at least one reaction product in the methanol synthesis effluent. In other aspects, the spacer layer can reduce the concentration of at least one reaction product from the methanol conversion effluent by 10% or more, or 20% or more. In some aspects, the deactivation can be further reduced or minimized by using an adsorbent as part of the spacer layer. Use of an adsorbent can allow for further reduction of the concentration of the at least one reaction product, such as reducing the concentration of at least one reaction product from methanol synthesis and/or methanol conversion by 30% or more, or 50% or more, such as up to substantially complete removal of the at least one reaction product. Examples of adsorbents can include boron carbide particles and boron oxide supported on alumina.

In this discussion, a layered catalyst grouping is defined as a series of layers corresponding to the multiple types of catalysts in the reactor plus spacer layers below each catalyst. As an example, a layered catalyst grouping for conversion of synthesis gas to dimethyl ether can correspond to a) a layer of metal catalyst (for methanol synthesis), b) a second spacer layer, c) a layer of acidic catalyst (for conversion of methanol to dimethyl ether), and d) a fourth spacer layer. The catalysts are listed in the order in which a feed would contact the layers within a reactor.

Reactions for Direct Synthesis of $C_{2+}$ Compounds from Synthesis Gas

One option for conversion of synthesis gas is to form dimethyl ether. Equations (1) and (2) show the stoichiometry for the conversion of synthesis gas to dimethyl ether.

$$3CO+3H_2 \Longleftrightarrow CH_3-O-CH_3+CO_2 \qquad (1)$$

$$CO+H_2O \Longleftrightarrow CO_2+H_2 \qquad (2)$$

Therefore, with a feed of 4 moles of CO, 3 moles of $H_2$, and 1 mole of $H_2O$, products can be formed corresponding to 1 mole of dimethyl ether (DME), 2 moles of $CO_2$, and 1 mole of $H_2$.

During one stage or direct synthesis of dimethyl ether from synthesis gas, a synthesis gas feed and steam can be introduced into the reactor. Synthesis gas corresponds to a mixture of $H_2$ and CO. For conversion of synthesis gas to dimethyl ether, a molar ratio of $H_2$ to CO in the synthesis gas of roughly 1.0 can be beneficial, such as a molar ratio of 0.5 to 2.0, or 0.7 to 1.4, but various ratios of $H_2$ and CO can be present depending on the source of the synthesis gas. The molar ratio of $H_2O$ (as steam) to CO can be 0.25 or more, or 0.5 or more. In aspects where the synthesis gas feed is derived from a reformer, some $CH_4$ may be present in the feed due to incomplete reforming. The synthesis gas feed can optionally also include $CO_2$ and $H_2O$, which correspond to the other equilibrium products that participate in the water gas shift reaction. Still other components that correspond to diluents may also be present, such as $N_2$.

As shown by Equations (1) and (2), the resulting effluent can include at least DME, $H_2$, and $CO_2$. If $CH_4$ is present in the feed to the reactor, the $CH_4$ can also pass through into the reaction effluent. Some additional unconverted CO and $H_2$ can also be present, as well as excess $H_2O$. Depending on the aspect, the reaction effluent can be separated in various manners. For example, the DME product can be separated from the effluent and then stored or passed to other reaction stages for further use. The $CO_2$ and/or $CH_4$ can be separated from the effluent for recycle back to the reforming stage. $H_2$ can be separated from the effluent and used as fuel, such as fuel for heating the reforming reactor. These separations can be performed using any convenient method. Such separations can include refrigeration, distillation/fractionation, and/or membrane separations to separate desired streams from the effluent.

In aspects where other products are generated from the synthesis gas, the inputs to the reactor can be similar, but the desired ratios may be different. For example, for conversion of synthesis gas to olefins, a $H_2$ to CO molar ratio of roughly 2.0 may be beneficial, such as a $H_2$ to CO ratio of 1.5 to 3.0, or 1.5 to 2.5. Additionally, introduction of steam may be optional, as stoichiometrically 2 moles of CO plus 4 moles of $H_2$ can be converted into 1 mole of $C_2H_4$ (ethene) and 2 moles of $H_2O$.

The reaction conditions in the reactor can vary depending on the nature of the desired product. For conversion of synthesis gas to dimethyl ether, the temperature can range from 200° C. to 300° C., or 200° C. to 270° C., with pressures between 20 bar and 50 bar (~2.0 MPa-g to ~5.0 MPa-g). For conversion of synthesis gas to olefins or aromatics, higher temperature conditions can be beneficial, such as temperatures of 250° C. to 350° C. for olefin production, or 300° C. to 450° C. for aromatics production. The conversion conditions can be effective for conversion of 30 mol % or more of the CO in the synthesis gas feed during a single pass through the reactor, or 35 mol % or more, or 40 mol % or more, such as up to 60 mol % or possibly still higher.

Spacer Layers, Spacer Particles, and Adsorbents

In various aspects, spacer layers can be included between methanol synthesis catalysts and methanol conversion catalysts in a reactor. In some aspects the spacer layers can be composed of inert particles. Inert particles correspond to particles with sufficiently low acidity to result in minimal or no conversion of methanol under the reactor conditions. Such inert particles can have an Alpha value of 5.0 or less, or less than 1.0, such as an Alpha value of substantially zero. Silica particles are an example of a suitable type of spacer particle. It is noted that particles that exhibit substantially no activity under the conditions of an Alpha test are defined as particles having an Alpha value of substantially zero.

The spacer particles can be of a convenient size for use in a fixed bed reactor, such as a trickle bed reactor. In some aspects, the spacer particles can have a size and/or characteristic dimension similar to the size and/or characteristic dimension of at least one of the types of catalyst particles.

When using in a layered catalyst configuration, the thickness of a spacer particle layers can be similar to or less than the thickness of the catalyst layers. In some aspects, the methanol synthesis catalyst layers can each have a first set of thicknesses (possibly the same or different for each layer), while the methanol conversion catalyst layers can have a second set of thicknesses (possibly the same or different for each layer). In such aspects, the thicknesses of the spacer layers can be selected based on the thickness of the adjacent catalyst layer upstream from the spacer layer. In such aspects, the thickness of the spacer layers can be 110% or less of the thickness of the adjacent catalyst layer, or 100% or less, or 90% or less, or 70% or less, or 50% or less, such as down to 10% or possibly still lower. Additionally or alternately, the "space velocity" of the feed relative to the spacer layers can be equal to or greater than the WHSV or GHSV in the catalyst layers, such as 10% or more greater, or 50% greater, or 100% greater. It is noted that the particles in the spacer layer are not catalyst particles, and therefore are not included in the space velocity calculation. However, for purposes of characterizing layer thickness, a spacer layer space velocity can be calculated for individual layers of the spacer particles.

In other aspects, the layers for the methanol synthesis catalyst and/or for the methanol conversion catalyst may vary in thickness, such as having thicker/thinner layers near the top of the reactor and thinner/thicker layers in downstream catalyst layers. In such aspects, the thickness of a spacer layer can be 100% or less of the thickness of the adjacent upstream catalyst layer, or 90% or less, or 70% or less, or 50% or less, such as down to 10% or possibly still lower.

Optionally, the particles in the spacer layer can at least partially correspond to particles that include an adsorbent. The adsorbent refers to a component that can further inhibit catalyst deactivation in the methanol synthesis catalyst layers and/or the methanol conversion catalyst layers. Boron compounds are an example of an adsorbent. The boron can be in the form of boron carbide particles, in the form of boron oxide supported on a carrier such as alumina, or in another form where the boron is stabilized/immobilized and will substantially remain in the spacer layer. In some aspects, a mixture of inert particles (such as silica) and boron-containing particles can be used.

The weight of spacer particles between the layers of catalyst can be similar to the weight of spacer particles when an adsorbent is not used. In aspects where the boron is provided as boron oxide supported on an oxide support, the amount of boron on the support can correspond to 1.0 wt % to 10 wt % of the weight of the oxide support. Additionally, the amount of support particles including boron can correspond to 25 wt % to 100 wt % of the particles in the spacer layer. When the boron corresponds to particles of boron carbide, the boron carbide particles can correspond to 1.0 wt % to 20 wt % of the particles in the spacer layer.

Figure 2:
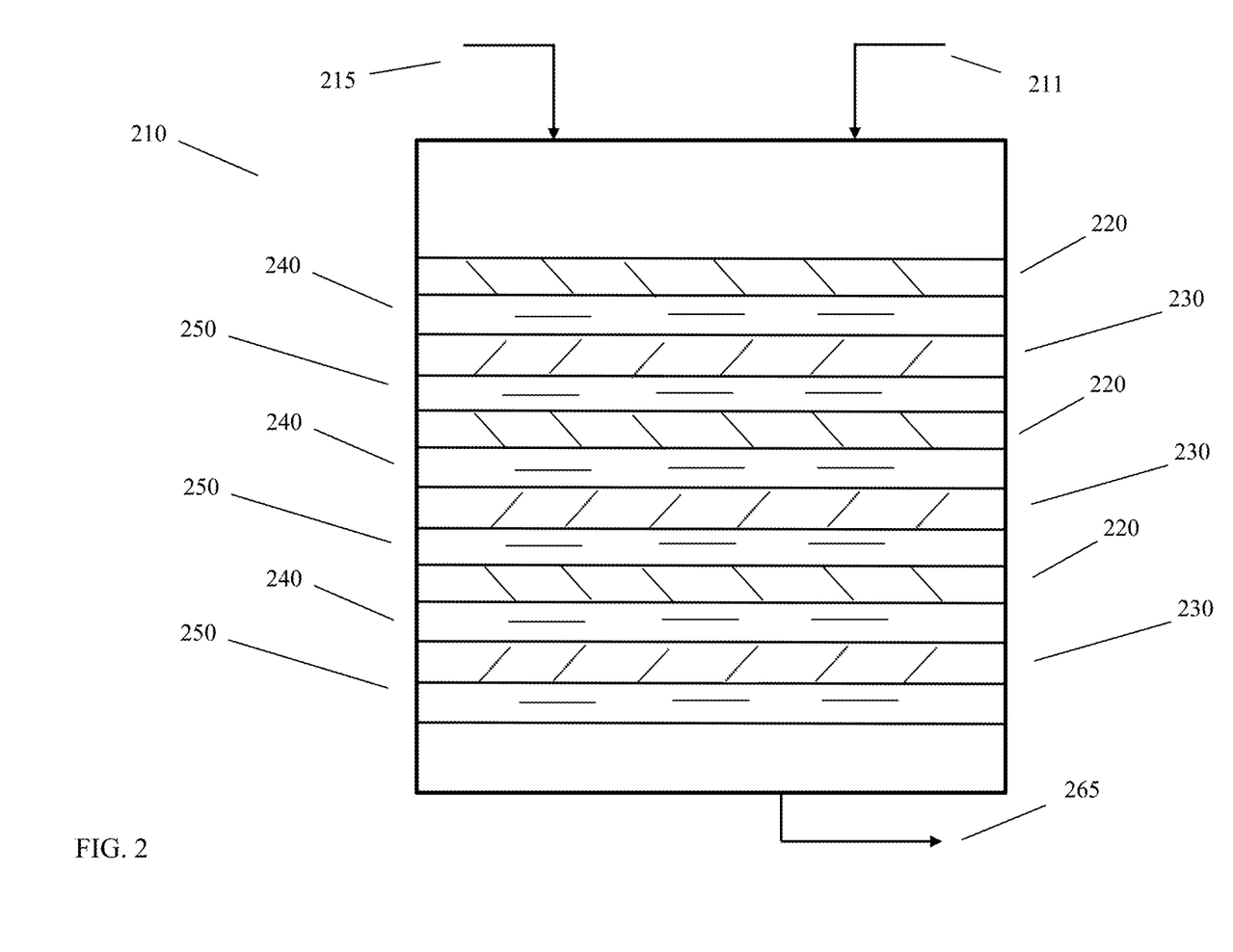
FIG. 2 shows an example of a layered catalyst arrangement for the conversion of synthesis gas to dimethyl ether.

FIG. 2 shows an example of a portion of a reactor that includes alternating layers of methanol synthesis particles and methanol conversion particles, with intervening spacer layers separating the two types of catalyst particles. In FIG. 2, reactor 210 receives a synthesis gas feed 215 and steam 211. The feed can pass down through the various layers in the reactor 210. The layers can include methanol synthesis catalyst layers 220, methanol conversion catalyst layers 230, and spacer layers 240 and 250. Spacer layers 240 correspond to spacer layers downstream from a methanol synthesis catalyst layer 220, while spacer layers 250 correspond to spacer layers downstream from a methanol conversion catalyst 230. FIG. 2 shows two layers each of methanol synthesis catalyst and methanol conversion catalyst, but any convenient number of layers can be present. After passing through the layers, an effluent 265 including dimethyl ether (and/or other conversion products) can be withdrawn from the reactor.

Catalysts

The methanol synthesis catalyst can be any convenient type of known methanol synthesis catalyst. Various combinations of copper, zinc, and aluminum as metals and/or metal oxides are known to be suitable for methanol synthesis, such as a combination of 60 wt % CuO, 30 wt % ZnO, and 10 wt % $Al_2O_3$. It is noted that although such a methanol synthesis catalyst is specified in oxide form, this is for convenience in describing the catalyst. The catalyst can be converted to a reduced form, including copper, zinc oxide, and aluminum oxide prior to use. Combinations of copper, zinc oxide, and aluminum oxide can also be suitable when operating the reactor at higher temperature, such as when performing conversion of synthesis gas to gasoline in a single reactor.

As an example, a methanol synthesis catalyst can include an oxide of one or more elements selected from the group consisting of copper, silver, zinc, boron, magnesium, aluminum, vanadium, chromium, manganese, gallium, palladium, osmium and zirconium. Optionally but preferably, at least one oxide can correspond to an oxide that is subsequently reduced to provide methanol synthesis activity.

In some aspects, the catalyst can be a copper based catalyst, such as in the form of copper oxide. In such aspects, the catalyst can further include an oxide of at least one element selected from the group consisting of silver, zinc, boron, magnesium, aluminum, vanadium, chromium, manganese, gallium, palladium, osmium and zirconium. Optionally but preferably, the catalyst can include copper oxide and an oxide of at least one element selected from the group consisting of zinc, magnesium, aluminum, chromium, and zirconium.

In yet other aspects, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various aspects, the methanol synthesis catalyst can include 10 wt % to 70 wt % copper oxide, based on total weight of the catalyst. In aspects where zinc oxide is present, the methanol synthesis catalyst can include 3 wt % to 30 wt % zinc oxide.

For the acidic catalyst, in some aspects related to production of dimethyl ether the acidic catalyst can correspond to an acidic porous material, such as alumina or silica-alumina. Other suitable materials can include, but are not limited to, amorphous heterogeneous lewis acid and/or Bronstead acid materials, such as mixed metal oxides corresponding to two or more oxides of Fe, Cu, Mn, W, and/or Zr. Such a catalyst can have an Alpha value of 1 or more, or 10 or more, such as up to 25 or possibly still higher. In other aspects, the acidic catalyst can correspond to an acidic porous material, such as alumina or silica-alumina, that is suitable for conversion of methanol to olefins and/or aromatics (such as conversion to gasoline). Such a catalyst can have an Alpha value of 1 or more, or 15 or more, or 20 or more, such as up to 200 or possibly still higher.

Additionally or alternately, the acidic catalyst can include a zeolite framework structure. In this discussion and the claims below, a zeolite is defined to refer to a crystalline material having a porous framework structure built from tetrahedra atoms connected by bridging oxygen atoms. Examples of known zeolite frameworks are given in the "Atlas of Zeolite Frameworks" published on behalf of the Structure Commission of the International Zeolite Association", 6$^{th}$ revised edition, Ch. Baerlocher, L. B. McCusker, D. H. Olson, eds., Elsevier, New York (2007) and the corresponding web site, http://www.iza-structure.org/databases/. Under this definition, a zeolite can refer to aluminosilicates having a zeolitic framework type as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework. It is noted that under this definition, a zeolite can include materials such as silicoaluminophosphate (SAPO) materials or aluminophosphate (AlPO) materials.

In some aspects, a zeolite with any convenient type of zeolite framework structure may be used. In such aspects, the zeolite can provide acidic activity, with little additional activity based on the framework structure. For example, at lower temperatures, a zeolite may function primarily as an acidic catalyst.

Generally, a zeolite having desired activity for methanol conversion can have a silicon to aluminum molar ratio of about 10 to about 200, or about 15 to about 100, or about 20 to about 80, or about 20 to about 40. For example, the silicon to aluminum ratio can be at least about 10, or at least about 20, or at least about 30, or at least about 40, or at least about 50, or at least about 60. Additionally or alternately, the silicon to aluminum ratio can be about 300 or less, or about 200 or less, or about 100 or less, or about 80 or less, or about 60 or less, or about 50 or less.

It is noted that the molar ratio described herein is a ratio of silicon to aluminum. If a corresponding ratio of silica to alumina were described, the corresponding ratio of silica ($SiO_2$) to alumina ($Al_2O_3$) would be twice as large, due to the presence of two aluminum atoms in each alumina stoichiometric unit. Thus, a silicon to aluminum ratio of 10 corresponds to a silica to alumina ratio of 20.

In some aspects, a zeolite in a catalyst can be present at least partly in the hydrogen form. Depending on the conditions used to synthesize the zeolite, this may correspond to converting the zeolite from, for example, the sodium form. This can readily be achieved, for example, by ion exchange to convert the zeolite to the ammonium form followed by calcination in air or an inert atmosphere at a temperature of about 400° C. to about 700° C. to convert the ammonium form to the active hydrogen form.

Additionally or alternately, a zeolitic catalyst can include and/or be enhanced by a transition metal. Preferably the transition metal is a Group 12 metal from the IUPAC periodic table (sometimes designated as Group IIB) selected from Zn, Cd, or a combination thereof. More generally, the transition metal can be any convenient transition metal selected from Groups 6-15 of the IUPAC periodic table. The transition metal can be incorporated into the zeolite/catalyst by any convenient method, such as by impregnation, by ion exchange, by mulling prior to extrusion, and/or by any other convenient method. Optionally, the transition metal incorporated into a zeolite/catalyst can correspond to two or more metals. After impregnation or ion exchange, the transition metal-enhanced catalyst can be treated in air or an inert atmosphere at a temperature of about 400° C. to about 700° C. The amount of transition metal can be expressed as a weight percentage of metal relative to the total weight of the catalyst (including any zeolite and any binder). A catalyst can include about 0.05 wt % to about 20 wt % of one or more transition metals, or about 0.1 wt % to about 10 wt %, or about 0.1 wt % to about 5 wt %, or about 0.1 wt % to about 2.0 wt %. For example, the amount of transition metal can be at least about 0.1 wt % of transition metal, or at least about 0.25 wt % of transition metal, or at least about 0.5 wt %, or at least about 0.75 wt %, or at least about 1.0 wt %. Additionally or alternately, the amount of transition metal can be about 20 wt % or less, or about 10 wt % or less, or about 5 wt % or less, or about 2.0 wt % or less, or about 1.5 wt % or less, or about 1.2 wt % or less, or about 1.1 wt % or less, or about 1.0 wt % or less.

A catalyst composition can employ a zeolite in its original crystalline form or after formulation into catalyst particles, such as by extrusion. A process for producing zeolite extrudates in the absence of a binder is disclosed in, for example, U.S. Pat. No. 4,582,815, the entire contents of which are incorporated herein by reference. Preferably, the transition metal can be incorporated after formulation of the zeolite (such as by extrusion) to form self-bound catalyst particles. Optionally, a self-bound catalyst can be steamed after extrusion. The terms "unbound" and "self-bound" are intended to be synonymous and mean that the present catalyst composition is free of any of the inorganic oxide binders, such as alumina or silica, frequently combined with zeolite catalysts to enhance their physical properties.

The zeolite catalyst can further be characterized based on activity for hexane cracking, or Alpha value. Alpha value is a measure of the acid activity of a zeolite catalyst as compared with a standard silica-alumina catalyst. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of about 538° C. and a variable flow rate as described in detail in the Journal of Catalysis, Vol. 61, p. 395. Higher alpha values correspond with a more active cracking catalyst. For an oxygenate conversion catalyst, Alpha values of at least 15 can be suitable, with alpha values greater than 100 being preferred. In particular, the Alpha value can be about 1 to about 1000, or about 1 to about 500, or about 1 to about 100.

As an alternative to forming self-bound catalysts, zeolite crystals can be combined with a binder to form bound catalysts. Suitable binders for zeolite-based catalysts can include various inorganic oxides, such as silica, alumina, zirconia, titania, silica-alumina, cerium oxide, magnesium oxide, yttrium oxide, or combinations thereof. For catalysts including a binder, the catalyst can comprise at least about 10 wt % zeolite, or at least about 30 wt %, or at least about 50 wt %, such as up to about 90 wt % or more. Generally, a binder can be present in an amount between about 1 wt % and about 90 wt %, for example between about 5 wt % and about 40 wt % of a catalyst composition. In some aspects, the catalyst can include at least about 5 wt % binder, such as at least about 10 wt %, or at least about 20 wt %. Additionally or alternately, the catalyst can include about 90 wt % or less of binder, such as about 50 wt % or less, or about 40 wt % or less, or about 35 wt % or less. Combining the zeolite and the binder can generally be achieved, for example, by mulling an aqueous mixture of the zeolite and binder and then extruding the mixture into catalyst pellets. A process for producing zeolite extrudates using a silica binder is disclosed in, for example, U.S. Pat. No. 4,582,815. Optionally, a bound catalyst can be steamed after extrusion.

Example 1

General System and Methodology

A laboratory scale isothermal fixed bed reactor was used to compare conversion of synthesis gas to dimethyl ether using a mixed catalyst system with conversion using various layered catalyst systems. The various catalyst systems were loaded into the reactor and exposed to feed metered in by pumps (for liquid reactants) or mass flow controllers (for gas phase reactants). To deliver reactants to the reactor, gas phase reactants were pre-heated in an evaporator, and then mixed with the evaporating liquids before entering the reactor. The effluent from the reactor was monitored using a gas chromatograph. The gas chromatograph included flame ionization detector and a thermal conductivity detector to allow for product identification.

For conventional catalyst loading, a mixture of a CuZnAl catalyst (60/30/10) and acidic alumina particles having an Alpha value of roughly 2.0 was loaded into the catalyst bed. The catalyst mixture included equal masses of the CuZnAl catalyst and the alumina catalyst. The catalyst particles were sized at 60-80 mesh. The catalyst corresponded to 50% of the mass of the bed. The other 50% of the volume corresponded to 80-120 mesh quartz sand particles as a diluent. The diluent particles were added for consistency with the layered catalyst loadings.

For the layered catalyst loadings, the CuZnAl catalyst was divided into two, four, or six portions having equal mass. The alumina catalyst was similarly divided into two, four, or six portions having equal mass. The diluent quartz sand particles were divided into twelve equal portions.

For the layered catalyst loadings, a layer of the acid catalyst (alumina) is loaded first, followed by a layer of the quartz sand particles as a spacer layer. To maintain the separate nature of the layers, a stainless steel mesh was placed on top of the spacer layer. A layer of the metal catalyst (CuZnAl) was then placed on top of the stainless steel mesh, followed by a spacer layer, followed by another stainless steel mesh. This process was repeated with alternating layers of the acid catalyst, spacer, metal catalyst, and spacer, until all of the catalyst layers and spacer layers were loaded into the reactor. This resulted in four, eight, or twelve total catalyst layers within the reactor. The top layer corresponded to the metal catalyst, which provides the methanol synthesis activity that is needed to start the reaction process. Due to the laboratory scale nature of the reactor, care was taken to avoid contacting the side walls of the reactor with the catalyst, so that mixing of the catalyst layers could be avoided.

After loading the catalyst mixture or the catalyst layers into the reactor, the catalysts were dried and activated in accordance with the typical instructions provided for the respective catalysts. After activation, the reactor was placed under a flow of $N_2$ while the reactor was heated to the desired reaction temperature. After reaching the desired temperature, the reactor was then pressurized and the reactant flows were introduced.

Example 2

Comparison of Mixed and Layered Catalyst Loadings

The activity for conversion of synthesis gas to methanol for a mixed catalyst bed and beds with four, eight, and twelve total layers of catalyst. The feed was designed to be representative of a potential synthesis gas feed. Per mole of feed, the feed included 0.4 moles of CO, 0.4 moles of $H_2$, 0.05 moles of $CO_2$, 0.05 moles of $H_2O$, and 0.1 moles of Ar (included as an internal standard). The feed was exposed to the various catalyst loadings at a temperature of 250° C., pressures of 3.0 MPa-g to 5.0 MPa-g, and a gas hourly space velocity of 1000 hr$^{-1}$ to 8000 hr$^{-1}$.

Figure 3:
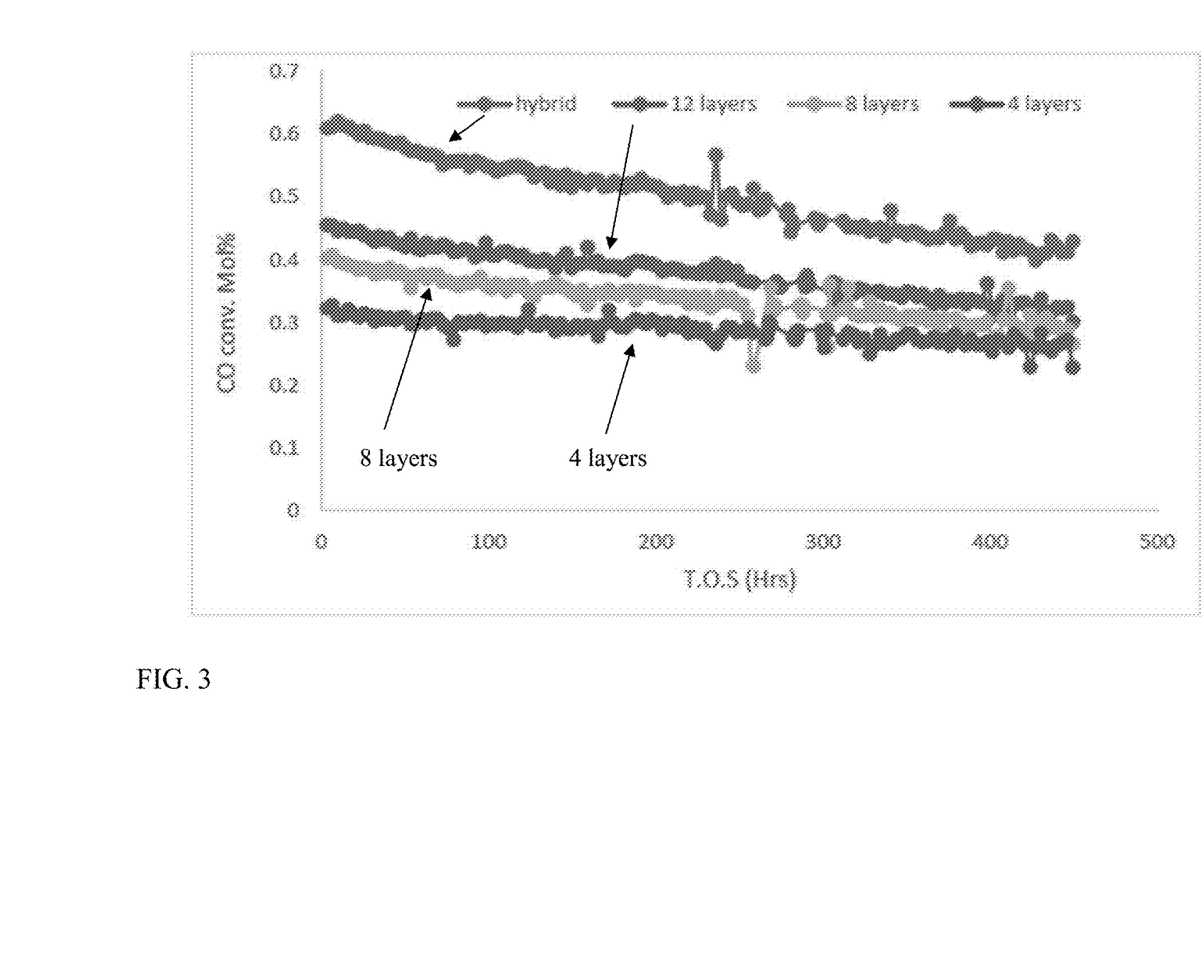
FIG. 3 shows conversion of CO using various arrangements of catalyst for conversion of synthesis gas to dimethyl ether.

FIG. 3 shows CO conversion activity for the various catalyst loadings at reaction conditions including a temperature of 250° C., a pressure of 3.5 MPa-g, and a gas hourly space velocity of 2600 hr$^{-1}$. As shown in FIG. 3, the mixed bed of catalyst initially provided roughly 60% conversion of the CO in the feed, but this decreased over time. The layered catalyst systems provided substantially lower conversion, but the decrease in conversion over time was reduced relative to the mixed bed. Additionally, increasing the number of catalyst layers from 4 to 8 and then to 12 resulted in successive increases in the amount of CO conversion. Based on the trends shown in FIG. 3, it was calculated that a layered catalyst bed including 16 catalyst layers would result in CO conversion activity similar to the mixed catalyst bed.

Figure 4:
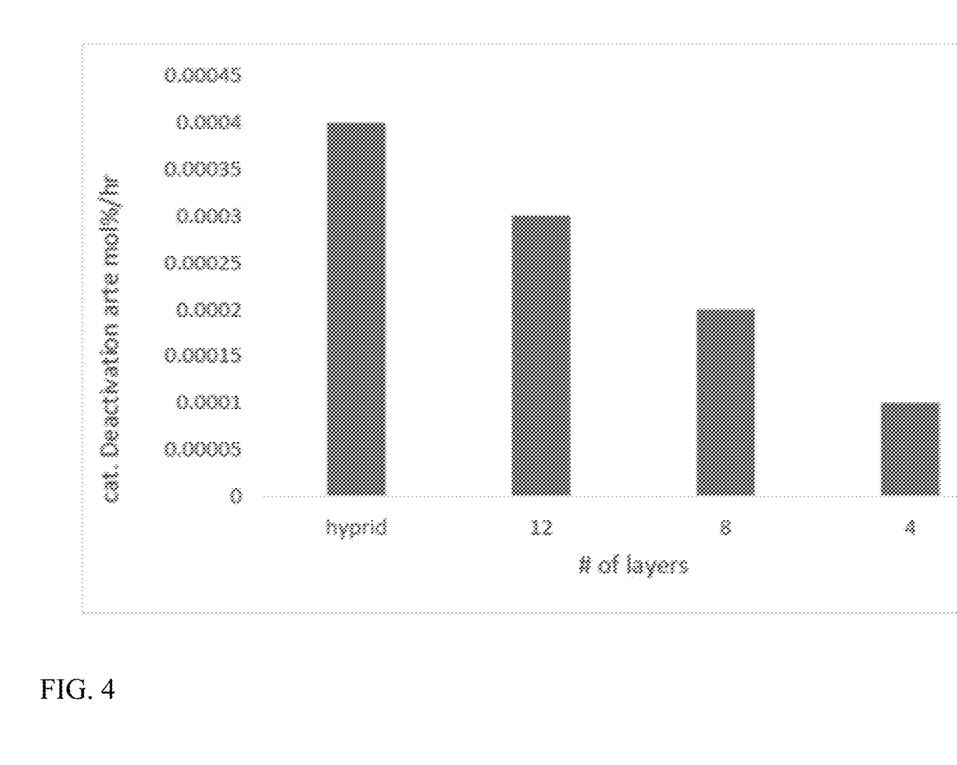
FIG. 4 shows the catalyst deactivation rate for various arrangements of catalysts for conversion of synthesis gas to dimethyl ether.

FIG. 4 shows a characterization of the catalyst deactivation rate. In FIG. 4, the average change in mole % conversion of CO per hour is shown versus the length of processing time. As shown in FIG. 4, the four catalyst layer configuration showed substantially lower catalyst deactivation than the mixed catalyst bed. As the number of layers increased, the catalyst deactivation rate increased. FIG. 4 demonstrates that by varying the catalyst layers, a desired process condition can be selected that balances the deactivation rate with the rate of conversion of CO to dimethyl ether (or another desired product).

Example 3

Adsorbent Examples

In order to reduce the deactivation rate of the catalyst, inclusion of boron as an adsorbent was investigated. The boron was believed to be suitable for binding with metals to reduce or minimize deposition of metals on the acidic catalyst.

Several types of boron addition methods were tested. A first type of boron addition corresponded to addition of boron oxide particles. A second type of boron addition corresponded to deposition of boric oxide on alumina by impregnating an alumina support with boric acid ($H_3BO_4$). A third type of boron addition corresponded to addition of boron carbide particles.

For addition of boron oxide particles, boron oxide particles sized to 80-120 mesh were used as the particles. For boron carbide, the particle size was roughly 200 mesh.

For boron supported on alumina, a commercial hydrotreating catalyst including less than 5 wt % of CoMo was used as the initial catalyst support. The hydrotreating catalyst was then impregnated with boric acid to produce catalyst particles with a boron oxide content of 1.8 wt %.

The feed and reaction conditions for the boron adsorbent tests were substantially the same as the feed and conditions used for Example 1.

Example 4

Addition of Boron Oxide Particles

A mixed catalyst bed as described in Example 1 was used for conversion of the model synthesis gas feed to dimethyl ether. For comparison, a second mixed catalyst bed was prepared where a portion of the quartz sand diluent particles were replaced with boron oxide. In this example, the gas hourly space velocity was 3200 hr$^{-1}$.

Figure 5:
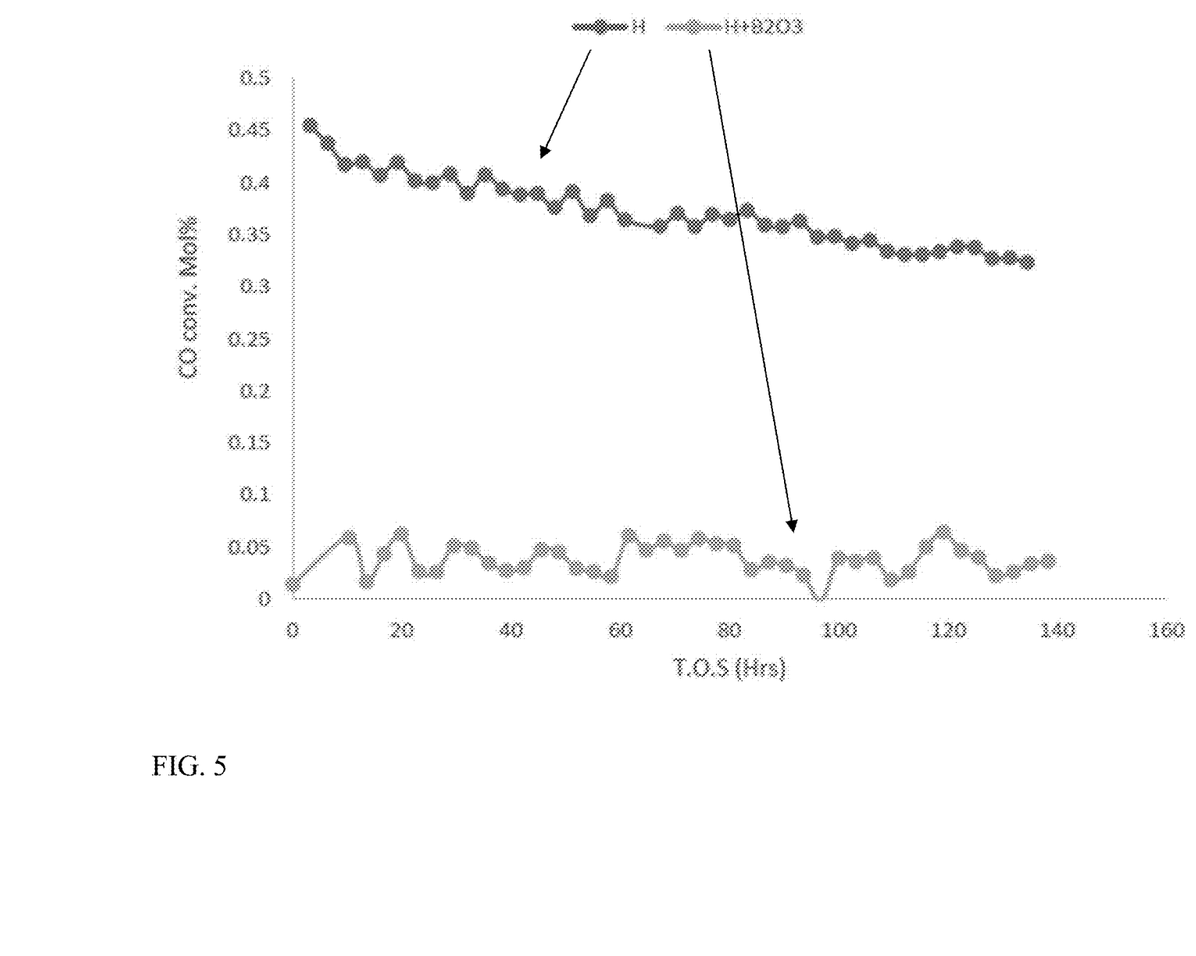
FIG. 5 shows conversion of CO as a function of time for a hybrid catalyst bed system with and without the inclusion of boron oxide particles in the catalyst bed.

FIG. 5 shows a comparison of the mole % of CO conversion for the baseline mixed catalyst system and the second mixed catalyst system where a portion of the diluent was replaced with the boron oxide particles. As shown in FIG. 5, the baseline mixed catalyst system showed steady deactivation of the catalyst over time, similar to the results observed in FIG. 3 for a mixed catalyst bed loading. By contrast, the mixed catalyst system that included the boron oxide particles exhibited an almost complete loss of CO conversion activity from the beginning of the characterization. It is believed that boron from the boron oxide particles can migrate within the reactor and bind with the metal catalyst, resulting in nearly complete deactivation of the metal catalyst.

Figure 6:
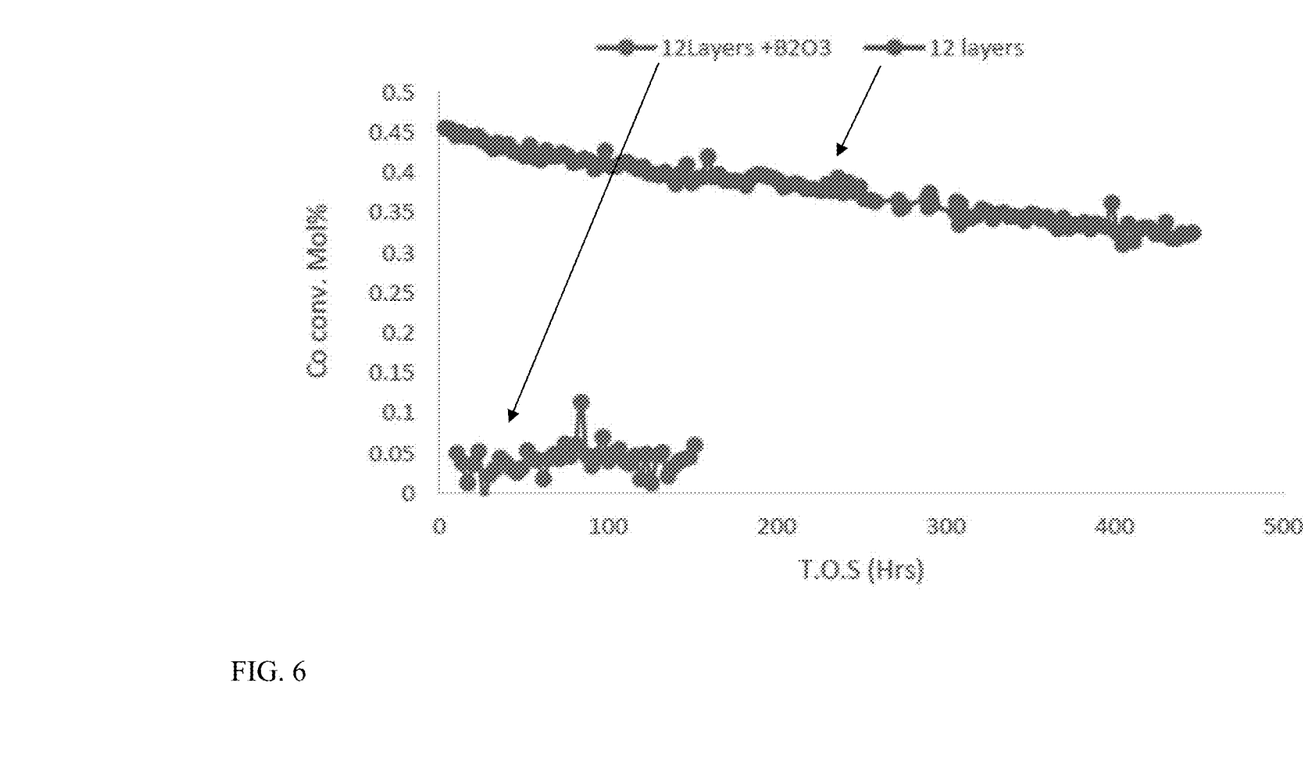
FIG. 6 shows conversion of CO as a function of time for a layered catalyst bed system with and without the inclusion of boron oxide particles in the layers.

Although it appeared that boron oxide particles resulted in a loss of catalyst activity, two additional tests were performed using a layered catalyst system that included 12 catalyst layers. One test used the quartz sand particles as the spacer layer. In the other test, the boron oxide particles were used as the spacer layer. FIG. 6 shows that this comparison resulted in a similar outcome to the results shown in FIG. 5. Once again, inclusion of the boron oxide particles into the layered catalyst system resulted in nearly complete deactivation of the metal catalyst.

Example 5

Supported Boron Oxide as Adsorbent

Figure 7:
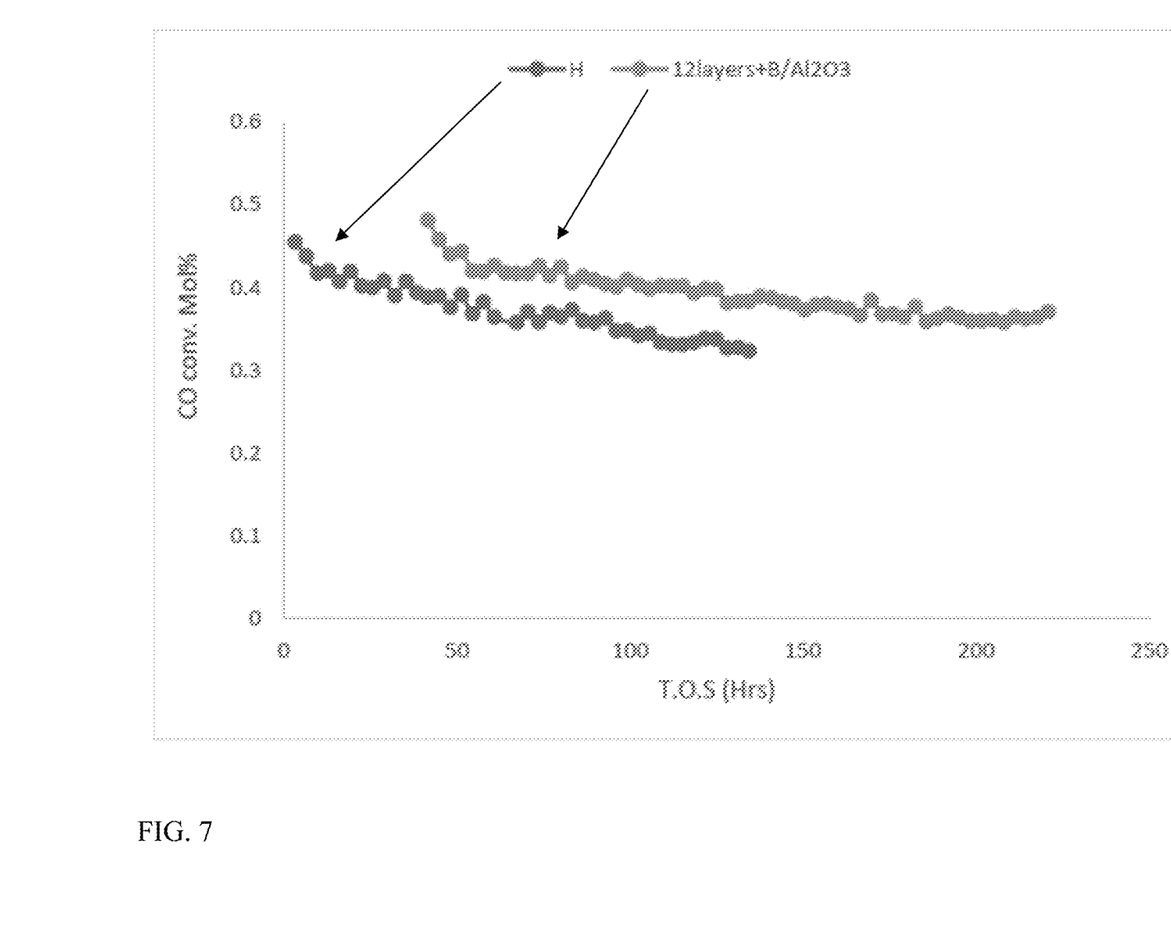
FIG. 7 shows conversion of CO as a function of time for a layered catalyst bed system with and without the inclusion of particles having boron supported on an alumina support in the layers.

In order to prevent migration of boron to the metal catalyst, a layered catalyst system including 12 catalyst layers was prepared where the particles in the spacer layers corresponded to 1.8 wt % $B_2O_3$ supported on the hydrotreating catalyst, as described in Example 3. Depositing the boron oxide on the catalyst support is believed to provide an "anchor" that can reduce or minimize migration of the boron oxide to the metal catalyst. FIG. 7 shows a comparison of the layered catalyst loading from FIG. 6 (no boron) with a layered catalyst loading corresponding to 12 catalyst layers and the supported boron oxide particles as the spacer particles. As shown in FIG. 7, the layered catalyst loading including the boron oxide particles as spacer particles unexpectedly provided improved catalyst activity as well as a reduction in the catalyst deactivation rate.

Example 6

Boron Carbide as Adsorbent

Figure 8:
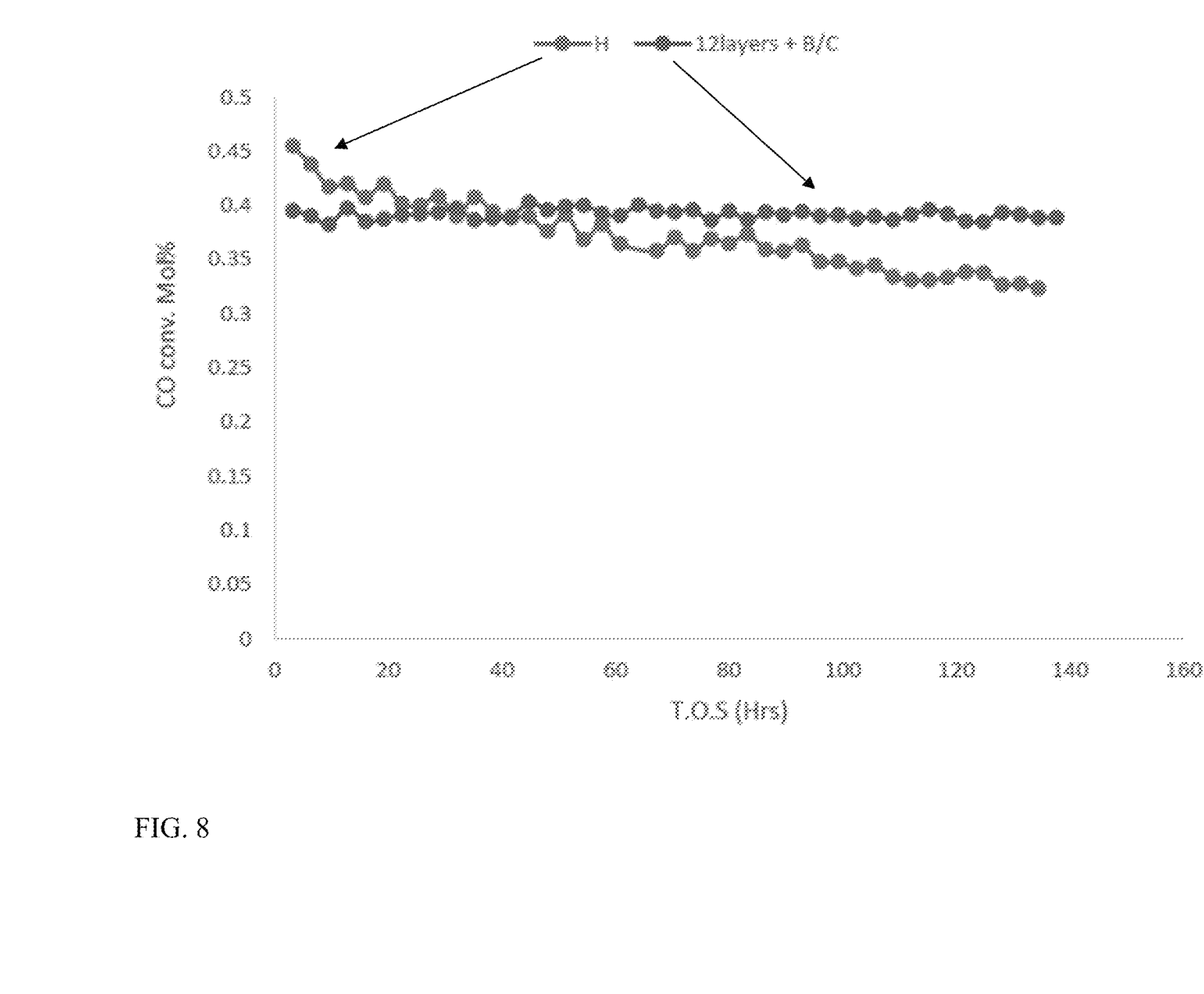
FIG. 8 shows conversion of CO as a function of time for a layered catalyst bed system with and without the inclusion of boron carbide particles in the layers

Another layered catalyst loading with 12 catalyst layers was prepared, but with boron carbide particles as the spacer particles. FIG. 8 shows a comparison of the layered catalyst loading from FIG. 6 (no boron) with a layered catalyst loading corresponding to 12 catalyst layers and the supported boron carbide particles as the spacer particles. As shown in FIG. 8, the behavior of the catalyst loading including the boron carbide particles was somewhat different from the behavior of the catalyst loading including supported boron oxide shown in FIG. 7. For the catalyst loading including the boron carbide, the initial CO conversion was lower than the 12 layer catalyst loading that did not include boron. However, the catalyst loading include boron carbide as the spacer particles exhibited almost no catalyst deactivation over the time period that was investigated. This unexpected improvement in maintaining catalyst activity could allow for extended operation of a reactor include a metal catalyst and an acid catalyst without requiring regeneration.

Additional Embodiments

Embodiment 1. A method for converting synthesis gas to $C_{2+}$ products, comprising: exposing a feed comprising CO and $H_2$ to a plurality of layered catalyst groupings under conversion conditions to form a conversion effluent comprising $C_{2+}$ products, each layered catalyst grouping comprising a) a methanol synthesis catalyst layer comprising methanol synthesis catalyst particles; b) a second spacer layer comprising second layer spacer particles; c) an acidic catalyst layer comprising acidic catalyst particles; and d) a fourth spacer layer comprising fourth layer spacer particles, wherein a combined weight of the methanol synthesis catalyst particles in the methanol synthesis catalyst layers comprises a first weight, a combined weight of the second layer spacer particles in the second spacer layers comprising 10% to 110% of the first weight, and wherein a combined weight of the acidic catalyst particles in the acidic catalyst particle layers comprises a third weight, a combined weight of the fourth layer spacer particles in the fourth spacer layers comprising 10% to 110% of the first weight.

Embodiment 2. A method for converting gas phase reactants in multiple steps, comprising: exposing a feed comprising CO and $H_2$ to a plurality of layered catalyst groupings under conversion conditions to form a conversion effluent comprising $C_{2+}$ products, the exposing of the feed to a layered catalyst grouping comprising: a) exposing the feed to a first catalyst layer comprising first catalyst particles under the conversion conditions to form a first intermediate effluent comprising a first plurality of reaction products, the first catalyst particles optionally comprising methanol synthesis catalyst particles; b) exposing the first intermediate effluent to a second spacer layer comprising second layer spacer particles under the conversion conditions to form a second intermediate effluent, a concentration of at least one reaction product of the plurality of reaction products in the second intermediate effluent being reduced by 10 wt % or more relative to a weight of the at least one reaction product in the first intermediate effluent; c) exposing the second intermediate effluent to a third catalyst layer comprising third catalyst particles under the conversion conditions to form a third intermediate effluent comprising a third plurality of reaction products, the conversion conditions being effective for conversion of one or more reaction products from the first plurality of reaction products to form the third plurality of reaction products, the third catalyst particles optionally comprising acidic catalyst particles; and d) exposing the third intermediate effluent to a fourth spacer layer comprising fourth layer spacer particles, a concentration of at least one reaction product of the third plurality of reaction products in the fourth intermediate effluent being reduced by 10 wt % or more relative to a weight of the at least one reaction product in the third intermediate effluent, wherein a combined weight of the first catalyst particles in the first catalyst layers comprises a first weight, a combined weight of the second layer spacer particles in the second spacer layers comprising 10% to 110% of the first weight, and wherein a combined weight of the third catalyst particles in the third catalyst layers comprises a third weight, a combined weight of the fourth layer spacer particles in the fourth spacer layers comprising 10% to 110% of the third weight.

Embodiment 3. The method of any of the above embodiments, wherein the feed is exposed to the plurality of layered catalyst groupings without intermediate separation.

Embodiment 4. The method of any of the above embodiments, wherein the plurality of layered catalyst groupings comprises 3 or more layered catalyst groupings, or wherein the plurality of layered catalyst groupings comprises 10 or less layered catalyst groupings, or a combination thereof.

Embodiment 5. The method of any of the above embodiments, wherein the acidic catalyst particles comprise an Alpha value of 1.0 or more, the acidic catalyst particles optionally comprising alumina, silica alumina, a mixed metal oxide, a zeolite, or a combination thereof.

Embodiment 6. The method of any of the above embodiments, wherein i) the conversion conditions comprise a temperature of 200° C. to 300° C. and a pressure of 2.0 MPa-g to 5.0 MPa-g, the $C_{2+}$ products comprising dimethyl ether; ii) the conversion conditions comprise a temperature of 250° C. to 350° C. and a pressure of 2.0 MPa-g to 5.0 MPa-g, the $C_{2+}$ products comprising $C_{2+}$ olefins; or iii) the conversion conditions comprise a temperature of 300° C. to 450° C. and a pressure of 2.0 MPa-g to 5.0 MPa-g, the $C_{2+}$ products comprising aromatic hydrocarbons.

Embodiment 7. The method of any of the above embodiments, wherein at least one of the second layer spacer particles and the fourth layer spacer particles comprise particles having an Alpha value of 5.0 or less, or less than 1.0.

Embodiment 8. The method of any of the above embodiments, wherein the second layer spacer particles are substantially the same as the fourth layer spacer particles.

Embodiment 9. The method of any of the above embodiments, wherein exposing the feed to a methanol synthesis catalyst layer further comprises forming a first intermediate effluent, the first intermediate effluent comprising an equilibrium amount of methanol based on the conversion conditions; or wherein exposing the feed to an acidic catalyst layer further comprises forming a third intermediate effluent, the third intermediate effluent comprising an equilibrium amount of at least one methanol conversion product based on the conversion conditions; or a combination thereof.

Embodiment 10. The method of any of Embodiments 1 or 3-9, wherein exposing the feed to a second spacer layer comprises: generating a first intermediate effluent from a methanol synthesis catalyst layer, the first intermediate effluent comprising a plurality of reaction products; and exposing the first intermediate effluent to the second spacer layer to form a second intermediate effluent, a concentration of at least one reaction product of the plurality of reaction products in the second intermediate effluent being reduced by 10 wt % or more relative to a weight of the at least one reaction product in the first intermediate effluent.

Embodiment 11. The method of any of Embodiments 1 or 3-10, wherein exposing the feed to a fourth spacer layer comprises: generating a third intermediate effluent from an acidic catalyst layer, the third intermediate effluent comprising a third plurality of reaction products; and exposing the third intermediate effluent to the fourth spacer layer to form a fourth intermediate effluent, a concentration of at least one reaction product of the third plurality of reaction products in the fourth intermediate effluent being reduced by 10 wt % or more relative to a weight of the at least one reaction product in the third intermediate effluent.

Embodiment 12. The method of any of the above embodiments, wherein at least one of the second layer spacer particles and the fourth layer spacer particles comprise adsorbent particles, the adsorbent particles comprising supported boron oxide particles, boron carbide particles, or a combination thereof.

Embodiment 13. The method of any of the above embodiments, wherein 30 mol % or more (or 35 mol % or more) of the CO in the feed is converted during the exposing to the plurality of layered catalyst groupings.

Embodiment 14. The method of any of the above embodiments, wherein the methanol synthesis catalyst layers comprise different weights of methanol synthesis catalyst particles, or wherein the acidic catalyst layers comprise different weights of acidic catalyst particles, or a combination thereof.

Embodiment 15. The method of any of the above embodiments, wherein a weight hourly space velocity of the feed relative to a methanol synthesis catalyst layer is 2.0 $hr^{-1}$ or more, or 5.0 $hr^{-1}$ or more; or wherein a weight hourly space velocity of the feed relative to an acidic catalyst layer is 2.0 $hr^{-1}$ or more, or 5.0 $hr^{-1}$ or more; or a combination thereof.

All numerical values within the detailed description and the claims herein are modified by "about" or "approximately" the indicated value, and take into account experimental error and variations that would be expected by a person having ordinary skill in the art.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for converting synthesis gas to $C_{2+}$ products, comprising:
    exposing a feed comprising CO and $H_2$ to a plurality of layered catalyst groupings under conversion conditions to form a conversion effluent comprising $C_{2+}$ products, each layered catalyst grouping comprising
        a) a methanol synthesis catalyst layer comprising methanol synthesis catalyst particles;
        b) a second spacer layer comprising second layer spacer particles;
        c) an acidic catalyst layer comprising acidic catalyst particles; and
        d) a fourth spacer layer comprising fourth layer spacer particles,
    wherein a combined weight of the methanol synthesis catalyst particles in the methanol synthesis catalyst layers comprises a first weight, a combined weight of the second layer spacer particles in the second spacer layers comprising 10% to 110% of the first weight, and
    wherein a combined weight of the acidic catalyst particles in the acidic catalyst particle layers comprises a third weight, a combined weight of the fourth layer spacer particles in the fourth spacer layers comprising 10% to 110% of the first weight.

2. The method of claim 1, wherein the feed is exposed to the plurality of layered catalyst groupings without intermediate separation.

3. The method of claim 1, wherein the plurality of layered catalyst groupings comprises 3 or more layered catalyst groupings, or wherein the plurality of layered catalyst groupings comprises 10 or less layered catalyst groupings, or a combination thereof.

4. The method of claim 1, wherein the acidic catalyst particles comprise an Alpha value of 1.0 or more.

5. The method of claim 1, wherein the acidic catalyst particles comprise alumina, silica alumina, a mixed metal oxide, a zeolite, or a combination thereof.

6. The method of claim 1, wherein the conversion conditions comprise a temperature of 200° C. to 300° C. and a pressure of 2.0 MPa-g to 5.0 MPa-g, the $C_{2-}$ products comprising dimethyl ether.

7. The method of claim 1, wherein the conversion conditions comprise a temperature of 250° C. to 350° C. and a pressure of 2.0 MPa-g to 5.0 MPa-g, the $C_{2-}$ products comprising $C_{2+}$ olefins.

8. The method of claim 1, wherein the conversion conditions comprise a temperature of 300° C. to 450° C. and a pressure of 2.0 MPa-g to 5.0 MPa-g, the $C_{2-}$ products comprising aromatic hydrocarbons.

9. The method of claim 1, wherein 30 mol % or more of the CO in the feed is converted during the exposing to the plurality of layered catalyst groupings.

10. The method of claim 1, wherein at least one of the second layer spacer particles and the fourth layer spacer particles comprise particles having an Alpha value of less than 1.0.

11. The method of claim 1, wherein the second layer spacer particles are substantially the same as the fourth layer spacer particles.

12. The method of claim 1, wherein exposing the feed to a methanol synthesis catalyst layer further comprises forming a first intermediate effluent, the first intermediate effluent comprising an equilibrium amount of methanol based on the conversion conditions.

13. The method of claim 1, wherein exposing the feed to an acidic catalyst layer further comprises forming a third intermediate effluent, the third intermediate effluent comprising an equilibrium amount of at least one methanol conversion product based on the conversion conditions.

14. The method of claim 1, wherein exposing the feed to a second spacer layer comprises:
    generating a first intermediate effluent from a methanol synthesis catalyst layer, the first intermediate effluent comprising a plurality of reaction products; and
    exposing the first intermediate effluent to the second spacer layer to form a second intermediate effluent, a concentration of at least one reaction product of the plurality of reaction products in the second intermediate effluent being reduced by 10 wt % or more relative to a weight of the at least one reaction product in the first intermediate effluent.

15. The method of claim 1, wherein exposing the feed to a fourth spacer layer comprises:
    generating a third intermediate effluent from an acidic catalyst layer, the third intermediate effluent comprising a third plurality of reaction products; and
    exposing the third intermediate effluent to the fourth spacer layer to form a fourth intermediate effluent, a concentration of at least one reaction product of the third plurality of reaction products in the fourth intermediate effluent being reduced by 10 wt % or more relative to a weight of the at least one reaction product in the third intermediate effluent.

16. The method of claim 1, wherein at least one of the second layer spacer particles and the fourth layer spacer particles comprise adsorbent particles.

17. The method of claim 1, wherein the adsorbent particles comprise supported boron oxide particles, boron carbide particles, or a combination thereof.

18. The method of claim 17, wherein 35 mol % or more of the CO in the feed is converted during the exposing to the layered catalyst groupings.

19. The method of claim 1, wherein the methanol synthesis catalyst layers comprise different weights of methanol synthesis catalyst particles, or wherein the acidic catalyst layers comprise different weights of acidic catalyst particles, or a combination thereof.

20. The method of claim 1, wherein a weight hourly space velocity of the feed relative to a methanol synthesis catalyst layer is 2.0 $hr^{-1}$ or more, or 5.0 $hr^{-1}$ or more; or wherein a weight hourly space velocity of the feed relative to an acidic catalyst layer is 2.0 $hr^{-1}$ or more, or 5.0 $hr^{-1}$ or more; or a combination thereof.

21. A method for converting gas phase reactants in multiple steps, comprising:
   exposing a feed comprising CO and $H_2$ to a plurality of layered catalyst groupings under conversion conditions to form a conversion effluent comprising $C_{2+}$ products, the exposing of the feed to a layered catalyst grouping comprising:
   a) exposing the feed to a first catalyst layer comprising first catalyst particles under the conversion conditions to form a first intermediate effluent comprising a first plurality of reaction products;
   b) exposing the first intermediate effluent to a second spacer layer comprising second layer spacer particles under the conversion conditions to form a second intermediate effluent, a concentration of at least one reaction product of the plurality of reaction products in the second intermediate effluent being reduced by 10 wt % or more relative to a weight of the at least one reaction product in the first intermediate effluent;
   c) exposing the second intermediate effluent to a third catalyst layer comprising third catalyst particles under the conversion conditions to form a third intermediate effluent comprising a third plurality of reaction products, the conversion conditions being effective for conversion of one or more reaction products from the first plurality of reaction products to form the third plurality of reaction products; and
   d) exposing the third intermediate effluent to a fourth spacer layer comprising fourth layer spacer particles, a concentration of at least one reaction product of the third plurality of reaction products in the fourth intermediate effluent being reduced by 10 wt % or more relative to a weight of the at least one reaction product in the third intermediate effluent
   wherein a combined weight of the first catalyst particles in the first catalyst layers comprises a first weight, a combined weight of the second layer spacer particles in the second spacer layers comprising 10% to 110% of the first weight, and
   wherein a combined weight of the third catalyst particles in the third catalyst layers comprises a third weight, a combined weight of the fourth layer spacer particles in the fourth spacer layers comprising 10% to 110% of the third weight.

22. The method of claim 21, wherein the first catalyst particles comprise methanol synthesis catalyst particles.

23. The method of claim 21, wherein the third catalyst particles comprise acidic catalyst particles.

* * * * *